United States Patent [19]

Pohl

[11] 4,265,634
[45] May 5, 1981

[54] CHROMATOGRAPHIC SEPARATION AND QUANTITATIVE ANALYSIS OF IONIC SPECIES

[75] Inventor: Christopher A. Pohl, Castro Valley, Calif.

[73] Assignee: Dionex Corporation, Sunnyvale, Calif.

[21] Appl. No.: 128,836

[22] Filed: Mar. 10, 1980

[51] Int. Cl.$^3$ ............... G01N 31/04; G01N 31/06; G01N 31/08
[52] U.S. Cl. ............... 23/230 R; 73/61.1 C; 210/656; 210/198.2; 422/70
[58] Field of Search ............... 23/230 R; 422/70; 210/31 C, 198 C; 73/61.1 C

[56] References Cited

U.S. PATENT DOCUMENTS

| | | | |
|---|---|---|---|
| 3,925,019 | 12/1975 | Small | 23/230 R |
| 3,926,559 | 12/1975 | Stevens | 23/230 R |
| 4,042,327 | 8/1977 | Haney | 210/31 C |
| 4,187,177 | 2/1980 | Stahl | 210/198 C |
| 4,199,323 | 4/1980 | Miller | 210/31 C X |

OTHER PUBLICATIONS

Chemical Abstracts, 91: 101564w (1979).
B. A. Allen et al., J. Chromatogr., 190, 241–245 (1980).

Primary Examiner—Sidney Marantz
Attorney, Agent, or Firm—Flehr, Hohbach, Test, Albritton & Herbert

[57] ABSTRACT

Method and apparatus for chromatographic separation and quantitative analysis of ions of like charges in a sample, e.g., cations or anions. For the analysis of inorganic anions, the sample and an eluent are directed to a hydrophobic chromatographic separation bed without permanently attached ion exchange sites. The eluent (a polar mobile liquid) includes an organic cation which reversibly adsorbs to the bed to create ion exchange sites which differentially retard the anions for chromatographic resolution. The eluent also includes a developing reagent of the same charge as the ion to be analyzed. The eluent including the resolved anions is then passed through an ion exchange resin which precludes passage of the counter ion and its co-ion in ionized form and then through a conductivity cell for quantitative detection. Inorganic cations may be detected in an analogous manner. The system may also be employed to analyze highly organic cations or anions (e.g., surfactants). In this instance, the organic ion of interest is already strongly attracted to the hydrophobic separation bed, and so the counter ion may be inorganic.

30 Claims, 4 Drawing Figures

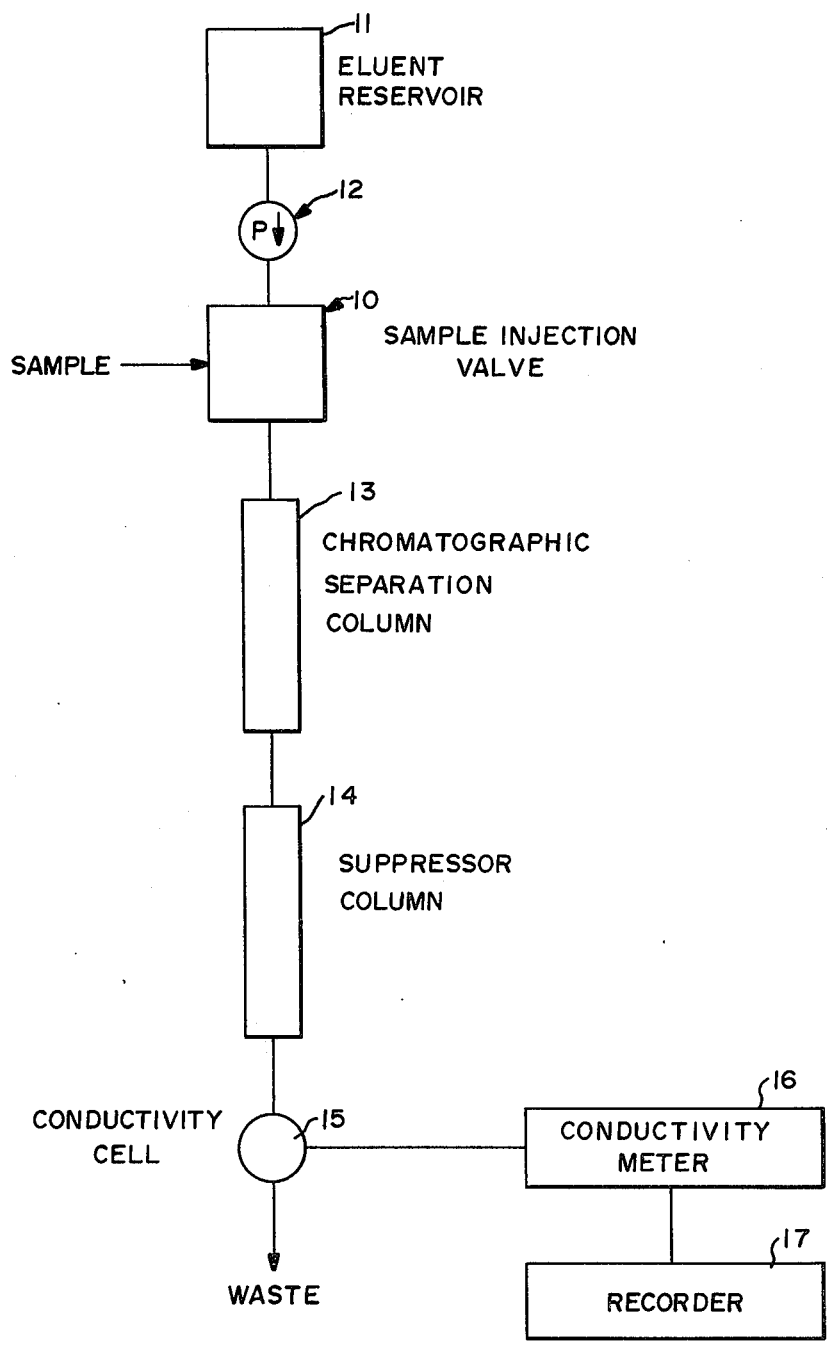
FIG.—1

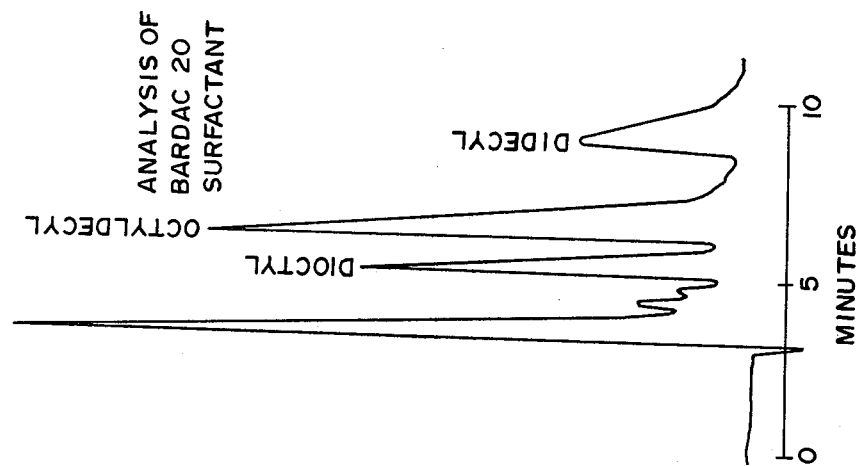
FIG.—4
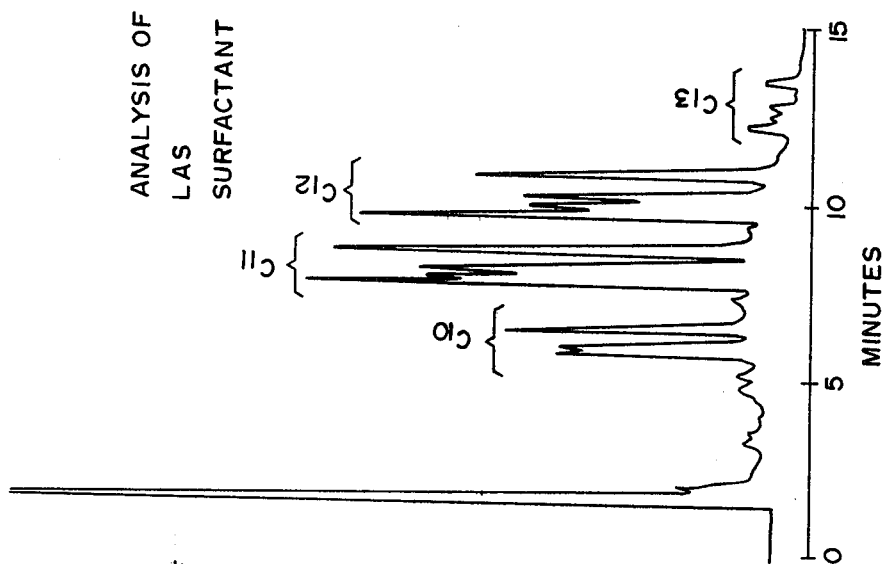
FIG.—3
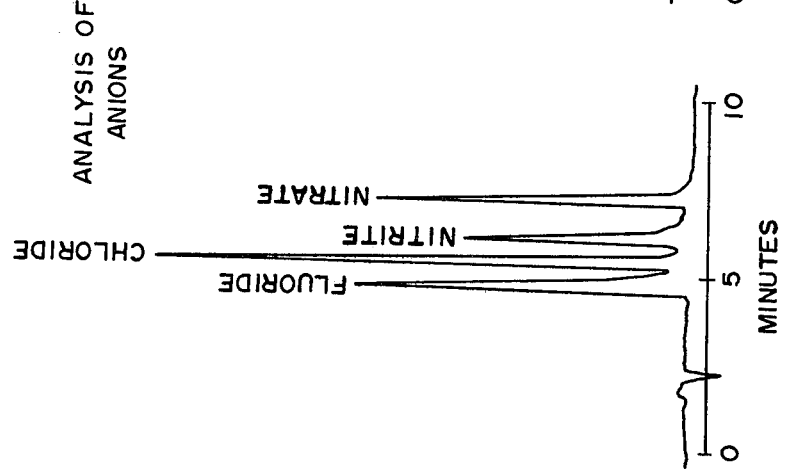
FIG.—2

CHROMATOGRAPHIC SEPARATION AND QUANTITATIVE ANALYSIS OF IONIC SPECIES

BACKGROUND OF THE INVENTION

The present invention relates to the quantitative analysis of different anions or cations in a single system. Reversed-phase liquid chromatography (RPLC) is widely used as a mode of separation in high performance liquid chromatography (HPLC). In RPLC, the mobile phase is more polar than the stationary phase, the reverse being true in conventional chromatography performed prior to development of RPLC. Chemically bonded hydrocarbon chains (alkyl groups) attached to silica substrates are one common form of stationary phase. The mode of formation of such stationary phases and suitable techniques for performing RPLC are well known as set out, for example, in N. H. C. Cooke and K. Olsen, *Am. Lab.*, 45 (August, 1979). One technique of RPLC has gained sufficient popularity to be called Reversed Phase Ion Pair Chromatography. In this technique, a salt is added to the mobile phase to improve the chromatographic properties. While there is some conflict in the theory of separation, the experimental techniques described in this paper are commonly employed. Specifically, the sample is directed in an aqueous polar mobile phase, commonly including a lower alcohol, acetonitrile or other water miscible organic solvent, together with a counter ion, typically tetrabutyl ammonium ion (TBA), for anion analysis. In one theory, hydrophobic ion pairs are formed which are relatively nonpolar and so are differentially retarded by the column. In another theory, the counter ion, e.g., TBA, is adsorbed to the surface to form a reversible ion exchange site on the stationary phase. This technique is employed primarily for the chromatographic separation and analysis of organic acids. However, typical detection techniques, such as ultraviolet detection, are unsuitable for the analysis of inorganics separated by RPLC. Also, for organic molecules, such as surfactants, the limit of ultraviolet detection does not provide for high sensitivity from lack of a strong chromaphore.

Another chromatographic system known as ion chromatography has been utilized in the quantitation of organic and/or inorganic anions and/or cations in aqueous sample solutions. In this technique, chromatographic separation is performed on low capacity ion exchange separating resin column or columns. Then the eluent is directed through a high capacity ion exchange resin suppressor column which converts the eluent from a conducting form to a non-conducting form and thereby reduces the background conductivity of the chromatographic system. The ions to be analyzed are eluted from the suppressor column and form highly conductive species which are passed through a conductivity cell and quantitated on the basis of conductivity. This technique is well suited to ionic species eluting from the suppressor column in a form which has a dissociation constant of greater than $10^{-7}$. Molecules with dissociation constants less than this are not detectable by conductivity at chromatographic concentration levels.

One limitation to ion chromatography is that the separating resin must be of a conventional permanent ion exchange site containing type. This substantially fixes both the ion exchange capacity and selectivity of the separating column since the ion exchange groups are chemically bonded to the substrate resin. Thus, for a given column and resin, modification of the chromatographic resolution would require chemical modification of the resin, such as by changing of the ion exchange groups by substituting a different type of resin, a time consuming and costly operation. The capacity of the separating resin must be small so that relatively low ionic strength eluents can be used to maximize suppressor column lifetimes. The resolution of highly ionized ionic species in accordance with this technique is set out, e.g., in Small et al. U.S. Pat. No. 3,920,397.

SUMMARY OF THE INVENTION AND OBJECTS

It is an object of the invention to combine the best features of the aforementioned prior art techniques of reverse phase paired ion chromatography and ion chromatography. Specifically, the ionic species to be separated are directed in a mobile phase through a first separating column comprising a porous hydrophobic chromatography bed with essentially no permanently attached ion exchange sites. This mobile phase also includes an ion exchange site-forming compound with a counter ion which reversibly adsorbs to the chromatographic substrate to create ion exchange sites and to cause the ionic species to be differentially retarded and chromatographically resolved in the eluent from the bed. The eluent also includes co-ions of the counter ions. Then the eluent is directed through a suppressor column including an ion exchange resin of a type which substantially precludes passage of excess counter ions and co-ions in ionic form. Finally, the eluent is directed through a conductivity cell having associated readout means to quantitatively detect the resolved ionic species. The mobile phase preferably includes substantially non-ionic organic polar compound and an inorganic developing ion, both of which can be employed to fine tune the column for optimum separation of the ions to be analyzed.

Another aspect of the invention revolves around a different theoretical mechanism. There, instead of the counter-ion of a site-forming compound forming a reversible adsorbed ion exchange site as set out above, the counter-ion and the ionic species form reversible ion pairs which are reversibly adsorbed onto the chromatographic bed for differential retardation and chromatographic resolution. Thereafter, the resolved species are directed through the suppressor column and conductivity cell as set forth above. This theory best explains the separation of long chain organic molecules, such as surfactants, which form the primary adsorptive bonds of the ion pairs. In fact, inorganic counter ions are preferable for use when analyzing such organic ionic species to permit desorption from the column in a reasonable period of time.

It is an object of the invention to provide a technique which combines the best features of reverse phase ion pair chromatography and ion chromatography.

It is a specific object of the invention to provide an ion chromatography technique in which the parameters of chromatographic selectivity and chromatographic capacity may be varied solely by changes in the eluent composition and concentration.

It is a specific object of this invention to couple this superior chromatographic separating technology with the superior detection system of ion chromatography which facilitates the highly selective and sensitive detection and quantitiation of ions with low $pK_a$ values.

It is a specific object of the invention to provide an optimization of ionic separation over a large range of selectivities by such eluent changes without rapid consumption of the suppressor column.

It is a further object of the invention to provide a technique for separation and detection of large organic ions which are difficult to accomplish by conventional ion chromatography and for which the detection limits of conventional reverse phase ion pair chromatography using ultraviolet or refractive index detection are inadequate.

Further objects and features of the invention will be apparent from the following description taken in conjunction with the accompanying drawings.

BRIEF DESCRIPTION OF THE DRAWINGS

FIG. 1 is a schematic representation of a simplified apparatus according to the present invention.

FIG. 2 is a chromatogram illustrating the separation of inorganic anions in accordance with the present technique.

FIGS. 3 and 4 are chromatograms illustrating the separation of the components of anionic surfactants and cationic surfactants, respectively, using the present technique.

DETAILED DESCRIPTION OF THE PREFERRED EMBODIMENTS

The system of the present invention is highly versatile, as it may be employed to determine a large number of strong and/or weak organic and/or inorganic ionic species so long as the species to be determined are solely cationic or anionic. Such ionic species are normally associated with counter ions but only ionic species of common charge are determinable by the present method. Suitable samples include surface waters, including salt water, and other liquids such as industrial chemical waste streams, body fluids such as serum and urine, beverages such as fruit juices and wines, and drinking water. Covalent molecular compounds, such as amines, which are convertible to ionic form as by forming acid salts are also analyzable in accordance with the present invention. When the term "ionic species" is used herein, it includes species in ionic form and components of molecules which are ionizable under the conditions of the present process.

Referring to FIG. 1, a simplified apparatus for performing the method of the present invention is illustrated. Sample is supplied to the system suitably by a syringe (not shown) at sample injection valve 10. The sample is carried through the system by eluent drawn from reservoir 11 by pump 12 which thereafter passes into chromatographic separation column 13 of a type to be described below. The eluent from column 13 passes through suppressor column 14 in which ions of opposite charge to the ions to be analyzed are substantially precluded from passage in ionic form. Typically, this occurs by stripping of such ions. Then the eluent containing the ionized ionic species flow through a liquid conduit to conductivity cell 15. The electrical signal emitted at cell 15, in which the fluctuation in ionic concentration produces an electrical signal proportional to that amount of ionic material registered by conductivity meter 16, is directed to recorder 17 which provides a visible readout for the signal from conductivity cell 15. After passing through the conductivity cell, the liquid is passed to waste.

The mode of separation in column 13 may be explained by two different theoretical mechanisms designated herein as the "paired ion" theory and the "reversible ion exchange" theory. Regardless of the prevailing theory, the system employs a mobile phase more polar in character than the stationary phase which carries a counter ion which interacts with the ionic species to be measured. This type of system is commonly referred to as a "reverse phase process." In early reverse phase work, the paired ion theory (as set out in the aforementioned Cooke and Olsen article) was assumed to be applicable, while some recent articles favor the other theory to be described in more detail below. It should be understood that the present invention is applicable to either or both theories, as it is the combination of using the reverse phase process for chromatographic separation together with the ion chromatographic technique for quantitating the separated ionic species that forms a major aspect of the present invention.

The method will first be described in accordance with the reversible ion exchange theory of separation. For simplicity of description, inorganic anions will first be described as the ionic species in the sample to be separated and quantitated in the system. The eluent in reservoir 11 which forms the mobile phase for the sample includes an ion exchange site-forming compound. This compound is comprised of a counter-ion of opposite charge to the ionic species and a co-ion of the same charge as the ionic species. (Herein, the term "counter ion" used alone refers to the last named counter ion and the term "co-ion" used by itself refers to the co-ion of that counter ion.) A porous hydrophobic chromatographic bed with essentially no permanently attached ion exchange sites is contained in separation column 13. This is to distinguish from conventional ion exchange resin in which the ion exchange sites are permanently attached by covalent bonding to the resin substrate.)

In accordance with the reversible ion exchange theory, the counter ion is of a type which forms reversible adsorptive bonds in situ in the chromatographic bed to create ion exchange sites therein. In this manner, the ionic species are differentially retarded by the thus formed ion exchange sites and are chromatographically resolved in the eluent from this bed. The inorganic anions to which the present technique is applicable includes essentially all types of anionic species from those weakly to strongly retained on the chromatographic bed. For example, the following anions may be separated: fluoride, chloride, nitrite, nitrate, chlorate, perchlorate, bromide, bromate, iodide, iodate, sulphate, thiosulphate, persulphate, pyrosulphate, phosphate, pyrophosphate, azide, cyanide, ferricyanide, and thiocyanate ions.

Certain chromatographic beds (e.g. silica-based ones) may be limited in their ability to separate specific ions which require extreme pH levels for adequate separation because the stationary phase cannot withstand such pH levels. Assuming that stationary phases are developed which are stable to such pH levels, the technique should be more versatile due to a wider range of mobile phases.

Referring to anionic analysis, suitable ion exchange site-forming compounds include: t-butylammonium hydroxide, mono-, di-, tri- and tetra-akyl ammonium hydroxide. The counter ions for inorganic anion analysis must be of opposite charge to the anions and be of a type capable of forming reversible adsorptive bonds with the chromatographic bed. This means that such counter ions must include organic chains, specifically alkyl chains, of sufficient length for ready adsorption on the column but not so long a chain as to be so firmly bound by the column as to be too difficult to remove in a reasonable period of time. Another parameter of the ion exchange site-forming compound of the present invention is that it must be capable of being substantially precluded from passage through suppressor column 14 in ionic form. As will be explained below, if the ion of interest is an anion, the suppressor column is cationic, and the counter ion is of a type which is removed or stripped by column 14. The co-ion of the counterion passes through the column but in substantially unionized form. Such co-ions include carbonate, borate and hydroxide, all of which form weakly ionized acids or water in the suppressor column. However, for those cases where silica comprises the chromatographic bed, hydroxide has limited utility due to dissolution of silica at higher pH levels.

The degree of adsorption of counter ion determines the column capacity which can be tailored to the desired retention time for a particular sample by controlling the amount of organic polar liquid. For example, it has been determined experimentally that the degree of adsorption of tetrabutyl ammonium hydroxide (TBAH) increases significantly as the organic polar liquid (e.g., acetonitrile) content decreases. The magnitude of TBAH adsorption is relatively small (e.g., 0.023 meq./ml. for 100 percent water eluent) compared to the exchange capacity of an ion exchange resin (e.g., 0.5 to 1.5 meq./ml.) Thus, the capacity of a reverse phase column in this mode is limited. Typically, the capacity of a system containing 0.004 molar TBAH is limited to about 2 to 4 micrograms of each ionic component per injection.

For the analysis of cations, the ion exchange forming compound must be of a type formed of a counter ion and co-ion which are capable of substantially being precluded from passage through the anionic ion exchange resin suppressor column maintained in hydroxide form. Suitable counter ions for this purpose include: lauryl sulphuric acid, $C_1-C_{20}$ alkyl sulphuric acid or sulphonic acid. The counter ions are retained on the column, while the co-ion, hydrogen, is removed as water molecules from suppressor column 14.

Any variety of reverse phase chromatographic separation stationary phases may be employed, as of the type illustrated in the aforementioned Cooke and Olsen article. Particularly effective chromatographic beds utilized for the stationary phase are hydrocarbon chains bonded to a substrate. Such chains are typically 8 to 18 carbons in length. Such chemically bonded alkyl phases are commonly produced by the reaction of surface silica silanols with organochlorosilanes. The type of chain may be varied, depending upon the ionic species of interest. Functionally, the bed provides uniform organic chain surfaces so that the counter ion is readily adsorbed onto the surface in a uniform repeatable manner. For this purpose, it is preferable to utilize a substrate with a relatively large specific surface area, e.g., 100 to 500 $m^2/g$. Organic resins such as polystyrene based ones with proper pore size distribution could also be employed for this purpose.

A typical bonded-phase porous silica gel packing is silica reacted with an organic material to bear an 18 carbon chain aliphatic group thereon. Such packing is sold by Waters Associates, Inc. under the trade designation Bondapak $C_{18}$. Other suitable resins are supplied by Altex Corporation and Merck & Co., Inc.

The mobile phase includes the sample and the counter ion in a polar aqueous liquid. The polar nature of the liquid facilitates ionization and dissolution of the ionic components of the system in the mobile phase.

Another preferable component of the mobile phase is a substantially non-ionic, organic polar compound in an amount which serves to selectively reduce the retardation time of the ionic species in the bed in a controlled manner. This organic polar compound is essentially non-ionic so as not to interfere with the ion conductivity measurement. Viewed one way, the organic compound serves as a mobile attractive force for the counter ions and, thus, the ionic species of interest to set up an equilibrium which removes these ions from the chromatographic column and passes them selectively into the mobile phase for separation. Viewed another way, the organic polar liquid competes with the organic counter ion for the available adsorptive binding sites on the stationary phase to cause a reduction in capacity of the same. In either event, a higher concentration of such organic polar compound shortens the retention time. Suitable organic polar compounds include lower alcohols, such as methanol and ethanol, acetonitrile, or any water miscible organic solvent.

The concentration and type of organic polar compound may be varied to a significant extent to modify the desired retention time, depending upon the ionic species to be analyzed. Suitable concentrations of such organic polar liquid can be varied from 0 to 100 percent, with the higher concentrations being employed for the more highly retained counter ions. At the upper limit there may be solubility problems for the ions of interest and so it is preferable to include water in the mobile phase. A further component of the mobile liquid phase is a developing reagent which includes an inorganic developing ion of the same charge as the ionic species. Such ion is included in an amount to selectively reduce the retardation time of the ionic species in the chromatographic bed. The developing ion and its co-ion (hereinafter termed the "co-ion of the developing ion") must be of a type which are substantially precluded from passage through suppressor column 14. Suitable developing ions include borate and carbonate ions. Both of these ions are converted by a suppressor column in the hydrogen ion form to their respective acids which are only weakly ionized and so do not provide substantial conductivity cell contaminating interference. Similarly, the co-ion of the developing ion are either stripped by the column or are in the hydrogen ion form which is the desired form of ionic species for detection in the conductivity cell.

The same principles apply for cation analysis. In this instance, suitable developing reagents include any of a variety of mineral acids, the anions of which are stripped by the suppressor column 14 to form water.

The developing reagent serves a similar function to developing reagents in conventional ion exchange separation in which the ion exchange sites are permanently attached to the resin substrate. That is, the developing reagents provide an equilibrium driving force which thereby displace the ionic species of interest from the stationary phase and, thus, shortens retention time.

The pH level of the eluent solution is another parameter which can affect the chromatographic separation in this technique which can be tailored to the ionic species of interest. However, extremes in pH level (e.g., levels about 2.0 or above about 7.5), which could facilitate certain separations, have a tendency to attack the silica based stationary phase. If a totally organic polymer chromatography bed were employed, this would obviate this problem.

Like the polar organic liquid, the type and concentration of developing reagent may be varied, depending upon the desired retention time. However, at high concentrations, the suppressor column may be rapidly depleted. Although the developing reagent is generally more useful for modifying selectivity and capacity of the separation bed than the polar organic liquid, its type and concentration must be carefully considered to avoid excessive depletion of the suppressor resin.

It is apparent from the foregoing that one of the significant advantages of the system is the ability to vary the developing reagent, polar organic liquid and counter ion to tune the system resolution to the specific ionic species to be analyzed.

Suppressor column 14 is analogous in function to stripper column 11 of FIG. 1 in Small et al. U.S. Pat. No. 3,920,297, which relates to ion chromatography. The principles of operation of that column, its detailed description and its relationship and functional characteristics with respect to the separation column are incorporated by reference at this point. Referring to the present system, column 14 is of relatively high specific capacity in comparision to separation column 13. This is because the primary function of this suppressor column is to preclude passage of the developing reagent and the ion exchange-site forming compound in highly ionized form while permitting passage of the ionic species resolved on separation column 13 without substantial interruption. Suitable ion exchange resins for analysis of anions are polystyrene or modified polystyrene cross-linked with divinylbenzene carrying nuclear groups, the latter providing reactive exchange sites. The strong cation exchange resins typically include nuclear sulphonic acid or sulphonate groups along the polymer chains while the weak cation exchange resins carry carboxylate groups.

The strong base anion exchange resins carry nuclear chloromethyl groups which have been quaternized. The weak base exchange resins carry nuclear primary, secondary or tertiary amine groups.

The nature of the resin in suppressor column 14 is determined by the ion exchange-site forming compound and developing reagent to be suppressed. For anion analysis, a suitable resin is a high cross-linked polystyrene including sulphonic groups in the hydrogen ion form. The high cross-linking assures that ion exchange effects predominate over chromatographic penetration into the resin. The counter ion and co-ion of the developing ion are modified by ion-exchange in the supressor to form products which elute from the column in substantially unionized molecular form and so which do not interfere with detection in the conductivity cell.

The effluent from suppressor column 14 is directed through conductivity cell 15 and then to a waste. The electrical signal from the conductivity cell is directed to the conductivity meter 16 and the output is directed to recorder 17.

The mechanism of separation is altered depending upon the nature of the ionic species to be analyzed. Specifically, as the sample ionic species become more hydrophobic (organic) in nature, the predominant mechanism is believed to become one of competitive adsorption between such ionic species and the counter ion in the eluent at the surface of the stationary phase in column 13. For example, alkyl chains of increasing length in the ionic species (e.g., surfactants) enter this competition. This results in unacceptable long retention and poor resolution. This problem can be obviated by changing the counter ions to a more hydrophilic inorganic ion. In general, as sample ionic species become more hydrophobic, it is preferable to utilize counter ions which are less hydrophobic to optimize chromatographic resolution of the ionic species. For example, ammonium ion may be used as the counter ion for anionic surfactant analysis, while perchlorate ion may be used as the counter ion for cationic surfactant separations. The suppressor column is still essential to reduce background conductivity of the counter ions.

For analysis of such highly hydrophobic ionic species, the paired ion mechanism is more likely to predominate. In this instance, rather than forming reversible ion exchange sites, the counter ion and ionic species form reversible ion pairs which, in turn, form reversible adsorptive bonds with the chromatographic bed for differential retardation of the ionic species on the bed. This is believed to be a major factor in the chromatographic resolution of the ionic species.

By way of emphasis, the choice of counter ions significantly affects the degree of adsorption of the ion pairs on the stationary phase. Specifically, the more highly organic a counter ion, i.e., the longer the carbon chain in the molecule, the more firmly retained is the counter ion and, thus, the ion pair. Thus, for inorganic ionic species, it is preferable to use highly organic counter ion compounds, e.g., $C_1$ to $C_{20}$ carbons long. Conversely, as set out below, for highly organic ionic species such as surfactants, it is preferable to use counter ion inorganic compounds to avoid excessive retention times.

The steps performed after separation according to the paired ion theory in the process are the same as those described above with respect to the reversible ion exchange theory. That is, after chromatographic separation, the eluent is passed through suppressor column 14 and then through conductivity cell 15 for measurement by conductivity meter 16 and visible readout on recorder 17.

It is a particular advantage of the present invention to provide a technique for analysis of anionic surfactants. While infrared spectroscopy and nuclear magnetic resonance techniques give some information regarding anionic surfactants, they are of limited value in determining the size and molecular weight distribution. Also, ion chromatography is not capable of analyzing organic surfactants.

To summarize, an overall significant advantage of the above system (in either the reversible ion exchange mode or paired ion mode) is the ability to modify the separation column's capacity (number of counter ions adsorped to the column's surface) and selectivity (relative retention of ionic species retained by such counter ions on the column) by varying the concentration and type of counter ion, developing reagent, and polar organic liquid to accommodate the type of sample to be analyzed. The system is so flexible that the same separation stationary phase may be converted to analyze cations or anions.

The eluent may be fixed for the entire run. In the alternative, the system is particularly well adapted to the use of continuously changing concentrations of reagents, commonly referred to as a gradient system. In the alternative, step changes in concentration may also be employed.

A further disclosure of the nature of the present invention is provided by the following specific examples of its practice. It should be understood that the data disclosed serve only as examples and are not intended to limit the scope of the invention.

EXAMPLE 1

This example relates to a separation and quantitation of inorganic anions, specifically, fluoride, chloride, nitrite and nitrate at concentrations of 100 ppm. The aqueous mobile phase includes a mixture including 0.0015 M TBAH, and 0.065 M boric acid dissolved in solvent comprised of 17 volumes acetonitrile and 83 volumes of $H_2O$. Flow rates were constant at 1.5 ml/min.

The mixture was directed to a chromatographic separation column 13 of dimension 15 cm by 4.6 mm packed with 5 micron Ultrasphere-IP packing, all supplied by Altex Corporation. After chromatographic resolution, the eluent was directed through a cation stripper, sized at 25 cm. by 4.1 packed ion exchange resin designated AGMP-50, sized at 200 to 400 mesh in the hydrogen form, supplied by Bio-Rad Corporation. Spent cation stripper columns could be regenerated by passing 200 ml. of 0.5 molar phosphoric acid through the column.

The mixture was then directed through the conductivity cell of a conductivity detector (Model 213 supplied by Wescan Instruments) with a cell constant of 30 $cm^{-1}$. The detector sensitivity was 30 $\mu$mho f.s. The chromatogram of this run is illustrated in FIG. 2.

In this instance, a relatively interference free separation is illustrated. The acetonitrile does not ionize and so passes the conductivity detector without interference. The tetrabutyl ammonium ion is retained by the suppressor column while the hydroxide passes as water. The boric acid developing reagent is relatively nonionized and so does not cause any substantial interference in the measurement of conductivity.

EXAMPLE 2

In this example, anionic surfactants were studied. Specifically, linear alkyl benzene sulphonate (LAS). The mobile phase included a counter ion containing compound $0.01N(NH_4)_3B_{10}O_{16}\cdot 8H_2O$ (ammonium borate) and 0.01 M boric acid to produce an aqueous mobile phase at a pH level of about 8.3. As in Example 1, retention of anionic surfactant was controlled by varying acetonitrile concentrations in the mobile phase while retaining the boric acid and ammonium borate levels at a constant. Flow rates were at 1.5 ml./min. The same chromatographic separation column and suppressor column and detector system as in Example 1 were employed. The detector sensitivity was 3 $\mu$mho f.s. Solvent A included the above concentrations of boric acid and ammonium borate in water while a solvent B included the same concentrations in a mixture of 75 parts by volume of acetonitrile to 25 parts by volume of water. The original solution included a 50/50 mixture of solvent A and solvent B while the final solution included 30 percent of solvent A and 70 percent of solvent B, at a gradient variation of 1 percent per minute. The resulting chromatogram is illustrated in FIG. 3.

Referring to FIG. 3, the first peak is likely unretained sulphate ion. The early minor peaks are probably $C_8$ and $C_9$ chain surfactant. There is an assumption with respect to the length of the carbon chains of the remainder of the peaks based upon normal distributions as no standards were available. The primary significance of the Example is the ability to rapidly separate and quantitate this complex mixture.

EXAMPLE 3

In this example, a cationic surfactant was analyzed, specifically a surfactant designated Bardac 20 (nominally a 1:2:1 molar mixture of dimethyldioctylammonium chloride: dimethyloctyldecylammonium chloride: dimethyldidecylammonium chloride).

In this instance, the reverse phase separation column was a 30 cm. by 4 mm. column packed with 10 micron $\mu$-Bondapack C-18 packing supplied by Waters Associates. (Although the analyte is a cationic surfactant, the same functional type of chromatographic separation bed is employed as in Example 2). A major difference in the apparatus from that of the previous examples is that an anionic suppressor column in the hydroxide form is employed, specifically a 25 cm. by 4.1 mm. column packed with Bio-Rad AGMP-1 200-400 mesh, in the hydroxide form during analysis. It is preferable to store the column in the chloride form for increasing storage life and to convert it to the hydroxide form just prior to use by passing 100 ml. of 1 molar sodium hydroxide through the column at 1 ml. per minute. In this instance, a mobile phase includes water and water-acetonitrile mixtures containing 0.0015 molar perchloric acid (counter ion compound) at a solution pH of about 2.3 in an aqueous mobile phase. Retention of the cation surfactant was controlled by varying the acetonitrile content of the mobile phase while holding the perchloric acid content constant. Flow rates were at 1.5 ml./min. After elution from the separation column, the mixture is passed through the suppressor column in the anionic form to remove the perchlorate ion and pass water only to avoid interference in the conductivity detector. The same detector system was used at a sensitivity of 0.1 $\mu$mho f.s. The test results are illustrated in FIG. 4 based on an assumption as to the time when the individual components would be removed from the column.

It is noted that the counter ion is inorganic to facilitate removal of the surfactants from the column. If both components of the ion pair were organic molecules, it would be difficult to drive the ionic species from the column in a reasonable analysis time.

What is claimed is:

1. The method of chromatographic separation and quantitative analysis of at least a first and second ionic species of ionizable compounds in a polar mobile liquid phase, all of said ionic species being of a positive or negative charge, comprising the steps of:

(a) directing said mobile liquid phase, including an ion exchange site-forming compound, through a first column including a porous, hydrophobic chromatographic bed with essentially no permanently attached ion exchange sites, said ion exchange-site forming compound including a counter ion of opposite charge to said ionic species and also including a co-ion of the same charge as said ionic species, so that said counter ion forms reversible adsorptive bonds with said chromatographic bed to create ion exchange sites therein, and so that said first and second ionic species are differentially retarded by said ion exchange sites and are chromatographically resolved in the eluent from said first column, said eluent also including counter ions and co-ions, (b) directing the eluent from said first column through a second column containing an ion exchange resin of a type which substantially precludes passage of said counter ions and co-ions in ionic form, and (c) directing the eluent from said second column through a conductivity cell having associated readout means to quantitatively detect said first and second ionic species.

2. The method of claim 1 in which said mobile liquid phase includes a substantially non-ionic, organic polar compound in an amount to reduce the retardation time of said ionic species in said bed in a controlled manner.

3. The method of claim 1 in which said mobile liquid phase includes a developing reagent, including an inorganic developing ion of the same charge as said ionic species, in an amount to reduce the retardation time of said ionic species in said bed in a controlled manner, the developing ion and its co-ion being of a type which are substantially precluded from passage through said second column in ionic form.

4. The method of claim 1 in which said chromatographic bed comprises a hydrocarbon chain bonded to a substrate forming a reversed-phase packing.

5. The method of claim 4 in which the substrate of the hydrocarbon chain comprises silica.

6. The method of claim 1 in which said ionic species are anions.

7. The method of claim 6 in which the co-ion of said counter ion is selected from the group consisting of hydroxide, borate and carbonate.

8. The method of claim 6 in which said second column is of a hydrogen-form cation exchange type which retains said counter ions and which passes the co-ions of said counter ions in hydrogen form.

9. The method of claim 6 in which said counter ion is an alkyl ammonium ion.

10. The method of claim 1 in which the ionic species are cations.

11. The method of claim 10 in which the co-ion of said counter ion is hydrogen.

12. The method of claim 10 in which said second column is of a hydroxide-form anion type which retains said counter ion and which passes the co-ions of said counter ion in hydroxide form.

13. The method of chromatographic separation and quantitative analysis of at least a first and second ionic species of ionizable compounds in a polar mobile liquid phase, all of said ionic species being of a positive or negative charge, comprising the steps of:

(a) directing said mobile liquid phase, including a counter ion of opposite charge to said ionic species and also including a co-ion of the same charge as said ionic species, through a first column including a porous, hydrophobic chromatographic bed with essentially no permanently attached ion exchange sites, so that said counter ion and ionic species form first and second reversible ion pairs which form reversible adsorptive bonds with said chromatographic bed, and so that said ionic species are differentially retarded by said bed and, thus, are chromatographically resolved in the eluent from said first column, said eluent also including a portion of said co-ions, (b) directing the eluent from said first column through a second column containing an ion exchange resin of a type which substantially precludes passage of said counter ions and co-ions in ionic form, and which converts the ionic species of said first and second ion pairs to a more highly ionized form, and (c) directing the eluent from said second column through a conductivity cell having associated readout means to quantitatively detect said first and second ionic species.

14. The method of claim 13 in which said mobile liquid phase includes a substantially non-ionic, organic polar compound in an amount to reduce the retardation time of said ionic species in said bed in a controlled manner.

15. The method of claim 13 in which said mobile liquid phase includes a developing reagent, including an inorganic developing ion of the same charge as said ionic species, in an amount to reduce the retardation time of said ionic species in said bed in a controlled manner, the developing ion and its co-ion being of a type which are substantially precluded from passage through said second column in ionic form.

16. The method of claim 13 in which said chromatographic bed comprises a hydrocarbon chain bonded to a substrate forming a reversed- phase packing.

17. The method of claim 16 in which the substrate of the hydrocarbon chain comprises silica.

18. The method of claim 13 in which said ionic species are anions.

19. The method of claim 18 in which the co-ion of said counter ion is selected from the group consisting of hydroxide, borate and carbonate.

20. The method of claim 18 in which said second column is of a hydrogen-form cation exchange type which retains said counter ions and which passes the co-ions of said counter ions in hydrogen form.

21. The method of claim 18 in which said counter ion is an alkyl ammonium ion.

22. The method of claim 13 in which the ionic species are cations.

23. The method of claim 13 which the co-ion of said counter ion is hydrogen.

24. The method of claim 13 in which said second column is of a hydroxide-form anion type which retains said counter ion and which passes the co-ions of said counter ion in hydroxide form.

25. The method of claim 13 in which said ionic species are organic and, compared to the counter ions in the ion pairs, form the predominant, reversible adsorptive bonds with said chromatographic bed.

26. The method of claim 13 in which said counter ion is inorganic.

27. The method of claim 13 in which said mobile liquid phase includes a substantially non-ionic, organic polar compound in an amount to reduce the retardation time of said ionic species in said bed in a controlled manner.

28. Apparatus for the chromatographic separation and quantitative analysis of species in a polar mobile liquid phase, including a common counter ion for said ionic species, all of said ionic species being of a positive or negative charge, said apparatus comprising:

(a) a first column containing a porous hydrophobic chromatographic bed with essentially no permanently attached ion exchange sites, said bed including hydrocarbon chains capable of forming reversible adsorptive bonds with organic moieties in said polar mobile liquid phase, (b) means for supplying said polar mobile liquid phase to said first column, (c) a second column containing an ion exchange resin bed of a type and capacity to substantially preclude passage of said counter ion in ionic form,
(d) first conduit means between first and second columns,
(e) conductivity measurement means and associated readout means, said measurement means including at least a first flowthrough conductivity cell, and
(f) second conduit means between said second column and said conductivity cell.

29. The apparatus of claim 28 in which said chromatographic bed comprises a hydrocarbon chain bonded to a substrate forming a reversed-phase packing.

30. The apparatus of claim 28 in which the substrate of the reversed phase comprises silica.

* * * * *